United States Patent [19]

Zirngibl et al.

[11] Patent Number: 4,474,956

[45] Date of Patent: Oct. 2, 1984

[54] PROCESS FOR THE PREPARATION OF 4-HYDROXY-2-METHYL-N-2-PYRIDYL-2H-1,2-BENZOTHIAZINE-3-CARBOXAMIDE 1,1-DIOXIDE

[75] Inventors: Ludwig Zirngibl, Zofingen; René Gnehm, Küngoldingen, both of Switzerland

[73] Assignee: Siegfried Aktiengesellschaft, Zofingen, Switzerland

[21] Appl. No.: 509,125

[22] Filed: Jun. 29, 1983

[30] Foreign Application Priority Data

Jul. 7, 1982 [CH] Switzerland ................. 4134/82

[51] Int. Cl.$^3$ ..................................... C07D 401/12
[52] U.S. Cl. .................................................. 544/49
[58] Field of Search ....................................... 544/49

[56] References Cited

U.S. PATENT DOCUMENTS

| | | | |
|---|---|---|---|
| 3,501,466 | 3/1970 | Rasmussen | 544/49 |
| 3,891,637 | 6/1975 | Lombardino | 544/49 |
| 4,100,347 | 7/1978 | Hammen | 544/49 |
| 4,309,427 | 1/1982 | Lombardino | 544/49 |

*Primary Examiner*—John M. Ford
*Attorney, Agent, or Firm*—Jordan and Hamburg

[57] ABSTRACT

In the preparation of 4-hydroxy-2-methyl-N-2-pyridyl-2H-benzothiazine-3-carboxamide 1,1-dioxide by reacting the corresponding 3-methoxycarbonyl compound with 2-aminopyridine, a dramatic increase in the yield is obtained if the reaction is carried out in the presence of 0.1 to 1.5 mole equivalent (based on the 3-methoxycarbonyl compound) of an alkyl- or arylsulfonic acid.

10 Claims, No Drawings

PROCESS FOR THE PREPARATION OF 4-HYDROXY-2-METHYL-N-2-PYRIDYL-2H-1,2-BENZOTHIAZINE-3-CARBOXAMIDE 1,1-DIOXIDE

The invention relates to a process for the preparation of 4-hydroxy-2-methyl-N-2-pyridyl-2H-1,2-benzothiazine-3-carboxamide 1,1-dioxide. This benzothiazine derivative, which has been disclosed under the INN name piroxicam, has become important in human therapy as an antiinflammatory agent.

Functional derivatives, obtained by amidation of the carboxyl group 2-alkyl-4-hydroxy-2H-1,2-benzothiazine-3-carboxylic acid 1,1-dioxides or the associated tautomeric 2-alkyl-3,4-dihydro-4-oxo-2H-1,2-benzothiazine-3-carboxylic acid 1,1-dioxides and the process leading to such carbamoyl compounds appear to have first been described in the patent applications relating to the priority of U.S. Pat. No. 3,501,466. The route taken in that process started from the N-(ethoxycarbonyl)-methyl derivative of saccharin and proceeded via a ring-extending reaction with the ethoxide ion, ammonolysis of the ethoxy carbonyl group thus formed in the 3-position and alkylation at the 2-position. Consequently, U.S. Pat. No. 3,591,584 described a large number of hitherto unknown 4-hydroxy-1,2-benzothiazine-3-carboxylic acid 1,1-dioxides or the corresponding 3-hydroxy-4-carboxylic acid compounds, substituted at various positions in the molecule, including the 2-methyl-N-2-pyridyl derivative mentioned at the outset, i.e. piroxicam. Two possible routes to these compounds were mentioned, of which the first proceeds via the reaction of a 4-hydroxy- or 3-hydroxy-2H-1,2-benzothiazine 1,1-dioxide with an isocyanate, and the other once again via ammonolysis or aminolysis of the alkoxycarbonyl group bonded at the 3- or 4-position, i.e. via a reaction which, in the case of the 2-methyl-N-2-pyridyl derivative mentioned at the outset, can be represented as follows:

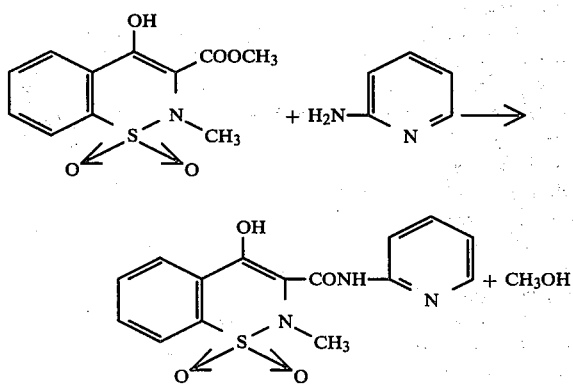

In view of the instability of the appropriate isocyanates, or the difficulty in obtaining these, the second route mentioned is to be used for the preparation of 3-carboxamides containing heterocyclic N-substituents, although the aminolysis process, in particular, is extremely delicate when carried out on an industrial scale. The β-ketocarboxylic acids are known to be unstable, undergoing decarboxylation, and the aminopyridine is likewise unstable under the reaction conditions, so that when this process is carried out in a conventional manner, the yields achieved are at best 45%, according to the literature (J. Med. Chem. 15, 849 (1972) and 16, 493 (1973)) and also according to our own investigations. To overcome this unsatisfactory situation, various routes have been taken. On the one hand, efforts have been made to obtain the end product directly by selective ring formation starting from N'-(2-methoxycarbonylbenzenesulfonyl)-N'-methyl-N-2-pyridyl glycinamide (U.S. Pat. Nos. 3,853,862 or re-issue 29,669), but in this procedure the advantage of the aminolysis process, of being able to obtain the intermediate readily, is once again lost. U.S. Pat. No. 3,891,637 describes a process in which the corresponding 3-carboxanilide (obtained from 4-hydroxy-2H-1,2-benzothiazine 1,1-dioxide and phenyl isocyanate) is converted to the pyridyl derivative by transamination, but in this procedure a further reaction stage with an additional loss in the yield has to be accepted.

Finally, U.S. Pat. Nos. 3,892,740 and 4,100,347 describe processes in which, either after intermediate conversion of the ketooxygen in the 4-position or of the 4-hydroxyl group to an alkoxy group, or while maintaining special conditions, the 3-alkoxycarbonyl group is hydrolyzed to a 3-carboxyl group and is then amidated to pyridyl carboxamide, after conversion to a reactive derivative, for example the acid chloride, or by means of a coupling promoter; once again, however, additional process stages have to be accepted and the yield (which according to the last-mentioned publication is 30%) is obviously not improved.

Surprisingly, we have now found that the preferred aminolysis process mentioned above can be improved by simple measures so that the yield assumes an order of magnitude of 75–80%, without this increase being at the expense of additional process stages. It has in fact been possible to establish that both the starting materials and the product in the reaction mixture are substantially stabilized by the presence of a sulfonic acid, provided that this is added in an amount of not less than 0.1 mole equivalent, based on the amount of methyl carboxylate to be reacted with the aminopyridine.

The invention accordingly relates to a process for the preparation of 4-hydroxy-2-methyl-N-2-pyridyl-2H-1,2-benzothiazine-3-carboxamide 1,1-dioxide by reacting methyl 4-hydroxy-2-methyl-2H-1,2-benzothiazine-3-carboxylate 1,1-dioxide with 2-aminopyridine, wherein the reaction is carried out in the presence of an alkyl- or arylsulfonic acid in an amount of 0.1 to 1.5 mole equivalent, based on the amount of the methoxycarbonyl starting material.

Examples of sulphonic acids suitable for this purpose are methanesulfonic acid, ethanesulfonic acid, benzenesulfonic acid and p-toluenesulfonic acid, and amounts of sulfonic acid of 0.3 to 0.7 mole equivalent, based on the methoxycarbonyl compound, have proved particularly effective. Parallel experiments under otherwise identical conditions gave a product yield of 39% in the absence of a sulfonic acid and a yield of 68% with 0.25 equivalent of methanesulfonic acid, while in contrast with 1.5 equivalent the yield was 62%, which was once again substantially below the maximum achievable. The stabilizing effect and the yield can furthermore be advantageously influenced if the sulfonic acid is added in portions or continuously over the entire duration of the reaction.

U.S. Pat. No. 3,591,584 cited at the outset does in fact indicate the advantage of adding sulfonic acid in a similar aminolysis reaction. Example XXI of that patent describes the reaction of 20.2 g of methyl 4-hydroxy-2- methyl-2H-1,2-benzothiazine-3-carboxylate 1,1-dioxide with 14 g of aniline to give the corresponding 3-carboxanilide, the reaction being carried out in the presence of 25 milligrams of p-toluenesulfonic acid and giving a yield of 35%. It should be noted that in this case the amount of sulfonic acid was less than 0.002 equivalent, based on the ester employed.

Neither this publication nor the remaining prior art contain any indications from which it would have been possible to derive the fact that the yield could be increased by a factor of almost 2 by increasing the amount of sulfonic acid by a factor of about 250. On the contrary, the relevant specialist literature (e.g. J.Org.Chem. 28, 2915 (1963) in fact recommends carrying out the aminolysis of carboxylic acid esters in the presence of basic catalysts, so that European Patent Application 3,360, page 11, also states that the reaction of esters of the type used according to the present invention with amines should be carried out "if required in the presence of a basic condensation agent".

The mechanistically still unexplained, advantageous effect on the aminolysis of the use, according to the invention, of a relatively large amount of sulfonic acid may therefore reasonably be regarded as being unforeseeable.

The reaction of the 3-methoxycarbonyl compound with the 2-aminopyridine is carried out in particular in an inert organic solvent, preferably in a lower N,N-dialkyl alkanamide or an aromatic hydrocarbon solvent. The alkyl radicals in the alkanamide preferably have up to 4 carbon atoms. The reaction is preferably carried out in dimethylformamide, dimethylacetamide, benzene, toluene or xylene, xylene being a particularly suitable solvent.

The reaction is preferably carried out in the temperature range between room temperature and the boiling point of the solvent, in particular in a stream of nitrogen.

Advantageously, the reaction is carried out using an excess of 2-aminopyridine, preferably using a molar amount of 2-aminopyridine which is 2 or 3 times the theoretically required equimolar amount. Advantageous results are obtained particularly when initially only a part of the total 2-aminopyridine to be employed is taken and the remainder of the total 2-aminopyridine to be employed is added in the course of the reaction, preferably in solid form.

The reaction can be carried out under reflux, but is preferably carried out while distilling off the solvent continuously and slowly.

When the reaction is complete, the major part of the residual solvent is distilled off rapidly, preferably in a vigorous stream of nitrogen, the remaining reaction mixture is cooled and an aqueous sulfonic acid solution is rapidly added or the reaction mixture is poured into such an aqueous sulfonic acid solution. In this procedure, it is preferable to use the same sulfonic acid as that added during the reaction. Thereafter, the mixture is cooled further, in particular in an ice-water bath, while stirring vigorously, and the product precipitated during this procedure is then filtered off. Washing and drying can, if required, be carried out in a conventional manner.

The example which follows is intended to illustrate the process of the invention in more detail.

EXAMPLE

In a 2.5 liter four-necked flask equipped with a mechanical stirrer, an internal thermometer, a descending condenser with a receiver protected by a drying tube, and a dropping funnel, the following substances are initially taken: 80.79 g (0.3 mole) of methyl 4-hydroxy-2-methyl-2H-1,2-benzothiazine-3-carboxylate, 1,1-dioxide, 42.34 g (0.45 mole) of 1-aminopyridine, 14.42 g (0.15 mole) of methanesulfonic acid and 1.8 liters of xylene (isomer mixture). The mixture is heated in an oil bath, while stirring, and about 150 ml of xylene, which contains traces of moisture, are initially distilled off in the course of about 1 hour, the distillate being discarded. Thereafter the bath temperature is lowered so that further solvent passes over very slowly (about 30–40 ml/hour). This distillate is replaced continuously by the dropwise addition of xylene from the dropping funnel. The progress of the reaction is monitored by means of thin-layer chromatography (precoated silica gel plates no. 5714 from Merck, mobile phase $CHCl_3$/isopropanol 98:2). 7 hours after the beginning of the reaction, 14.1 g (0.15 mole) of solid 2-aminopyridine are added in portions. 20 hours after the beginning of the reaction, about 800 ml of solvent are distilled off rapidly, i.e. in the course of about 1 hour, this procedure advantageously being carried out in a vigorous stream of nitrogen.

The reaction mixture is then cooled to an internal temperature of 60° C., and a solution of 43.2 g (0.45 mole) of methanesulfonic acid in 750 ml of water is allowed to run in rapidly. The vigorously stirred mixture is cooled further in the ice-water bath for at least 2 hours, after which it is filtered under suction and the residue is rinsed and dried in a through-circulation drier for not less than 20 hours at 55° C. 77.0 g of a beige product of melting point 191.5°–193.5° C. is obtained; according to thin-layer chromatography, this product no longer contains any of the educts. The yield is hence 0.232 mole or 77.4% of theory.

We claim:

1. A process for the preparation of 4-hydroxy-2-methyl-N-2-pyridyl-2H-1,2-benzothiazine-3-carboxamide 1,1-dioxide by reacting methyl 4-hydroxy-2-methyl-2H-1,2-benzothiazine-3-carboxylate 1,1-dioxide with 2-aminopyridine, wherein the reaction is carried out in the presence of an alkyl- or arylsulfonic acid in an amount of 0.1 to 1.5 mole equivalent, based on the amount of the methoxycarbonyl starting material.

2. The process as claimed in claim 1, wherein methanesulfonic acid or ethanesulfonic acid is used as the alkylsulfonic acid.

3. The process as claimed in claim 1, wherein benzenesulfonic acid or a toluenesulfonic acid is used as the arylsulfonic acid.

4. The process as claimed in claim 1, wherein the sulfonic acid is used in an amount of 0.5 to 1.0 mole equivalent, based on the methoxycarbonyl compound.

5. The process as claimed in claim 1, wherein the sulfonic acid is added in portions, spread over the entire duration of the reaction.

6. The process as claimed in claim 1, wherein the reaction is carried out in an inert organic solvent in the temperature range between room temperature and the boiling point of the solvent.

7. The process as claimed in claim 6, wherein the inert organic solvent is a lower N,N-dialkyl alkanamide, in particular dimethylformamide or dimethylacetamide, or an aromatic hydrocarbon, in particular benzene, toluene or xylene.

8. The process as claimed in claim 1, wherein the reaction mixture is substantially evaporated down after the end of the reaction by rapidly distilling off the solvent, and the product is precipitated by rapidly adding an aqueous sulfonic acid solution or pouring the reaction mixture into an aqueous sulfonic acid solution, in particular an aqueous solution of the sulfonic acid which has been added during the reaction.

9. The process as claimed in claim 1, wherein the reaction is carried out using a molar excess of 2-aminopyridine, in particular a two-fold or three-fold molar amount of 2-aminopyridine.

10. The process as claimed in claim 5, wherein the 2-aminopyridine is added in solid form.

* * * * *